US008921342B2

(12) United States Patent
Isogai et al.

(10) Patent No.: US 8,921,342 B2
(45) Date of Patent: Dec. 30, 2014

(54) LIVER FUNCTION-PROTECTING AGENT

(75) Inventors: Tomoyuki Isogai, Saitama (JP); Yukio Kadooka, Saitama (JP); Reo Tanaka, Saitama (JP); Akira Tomizawa, Saitama (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 509 days.

(21) Appl. No.: 12/811,744

(22) PCT Filed: Jan. 15, 2009

(86) PCT No.: PCT/JP2009/050408
§ 371 (c)(1),
(2), (4) Date: Jul. 6, 2010

(87) PCT Pub. No.: WO2009/090970
PCT Pub. Date: Jul. 23, 2009

(65) Prior Publication Data
US 2010/0279985 A1 Nov. 4, 2010

(30) Foreign Application Priority Data
Jan. 15, 2008 (JP) ................................. 2008-005162

(51) Int. Cl.
| | | |
|---|---|---|
| A61K 35/20 | (2006.01) | |
| A61K 47/24 | (2006.01) | |
| A61K 31/7032 | (2006.01) | |
| A23L 1/30 | (2006.01) | |
| A23L 2/52 | (2006.01) | |
| A23K 1/16 | (2006.01) | |

(52) U.S. Cl.
CPC ................ *A23L 1/30* (2013.01); *A23L 1/3006* (2013.01); *A61K 31/7032* (2013.01); *A61K 35/20* (2013.01); *A23L 2/52* (2013.01); *A23K 1/164* (2013.01)
USPC ............................................ 514/121; 554/79

(58) Field of Classification Search
CPC .... A61K 35/20; A61K 47/24; A61K 31/7032
USPC ............................................ 514/121; 554/79
See application file for complete search history.

(56) References Cited

U.S. PATENT DOCUMENTS 5,010,059 A 4/1991 Schmidt et al.

8,030,348 B2 * 10/2011 Sampalis ...................... 514/506
2009/0253658 A1 10/2009 Tanaka et al.

FOREIGN PATENT DOCUMENTS

| | | |
|---|---|---|
| CA | 2648653 | 10/2007 |
| JP | 62-5920 | 1/1987 |
| JP | 64-22893 | 1/1989 |
| JP | 2-250834 | 10/1990 |
| JP | 3-99091 | 4/1991 |
| JP | 5-279379 | 10/1993 |
| JP | 9-194362 | 7/1997 |
| JP | 10-17476 | 1/1998 |
| JP | 2000-336038 | 12/2000 |
| JP | 2001-275614 | 10/2001 |
| JP | 2002-68998 | 3/2002 |
| JP | 2002-226394 | 8/2002 |
| JP | 2002-275072 | 9/2002 |
| JP | 2004-99563 | 4/2004 |
| JP | 2004-346065 | 12/2004 |
| JP | 2005-112846 | 4/2005 |
| JP | 2006-306792 | 11/2006 |
| JP | 2006-311853 | 11/2006 |
| JP | 2007-110904 | 5/2007 |
| JP | 2007-291078 | 11/2007 |
| WO | 2007/138574 | 12/2007 |

OTHER PUBLICATIONS

Extended European Search Report dated Dec. 15, 2010 that issued with respect to counterpart European Patent Application No. 09701860.0.
Examination Report issued with respect to New Zealand Patent App. No. 586423, dated Mar. 9, 2011.
Mel'nichuk, D.O. et al., "A Comparative . . . Akademii Nauk Ukraini", A0110Biai, Dec. 2007, pp. 173-176.
New Zealand Office Action issued with respect to counterpart New Zealand Application No. 586423, dated Oct. 4, 2012.

* cited by examiner

*Primary Examiner* — Renee Claytor
(74) *Attorney, Agent, or Firm* — Greenblum & Bernstein, P.L.C.

(57) ABSTRACT

Disclosed is a liver function-protecting agent which comprises a phospholipid as an active ingredient, and which can exhibit an excellent prophylactic and ameliorating effect on the deterioration in the liver function when ingested orally. Also disclosed is a liver function-protecting food, beverage or feed. The phospholipid is preferably one derived from milk or a milk material. Alternatively, the phospholipid may be used in the form of a phospholipid-containing composition prepared from milk or a milk material and containing the phospholipid in an amount of 10 wt % or more relative to the total solid content.

6 Claims, No Drawings

LIVER FUNCTION-PROTECTING AGENT

TECHNICAL FIELD

The present invention relates to a liver function-protecting agent that includes a phospholipid as an active ingredient, and may easily and conveniently prevent or ameliorate a decrease in liver function via oral intake, and a liver function-protecting food, drink, or feed that comprises the liver function-protecting agent.

BACKGROUND ART

The liver is an animal internal organ that plays a very important role, and is involved in various biological reactions, such as metabolism, detoxication, digestion, energy storage and the like as the functions thereof. The liver has a high regeneration capability as compared with other internal organs, and completely regenerates even if part thereof has been removed by surgery or the like. However, even though a mild liver disease occurs, subjective symptoms may not appear, and a very serious life-threatening condition, such as fatty liver, cirrhosis or the like, may have often been reached when a patient becomes aware of the symptoms. Therefore, liver may be referred to as a silent organ.

Liver diseases are mainly caused by viruses. It is generally known that adult chronic hepatitis may be caused by alcohol consumption. A decrease in liver function has been mainly prevented or ameliorated by dietary restriction or administration of drugs. However, dietary restriction may be accompanied by mental difficulty, and incorrect dietary restriction may cause trophopathy. On the other hand, various drugs, such as glutathione, interferon or the like, have been administrated, but it requires taking account of side effects as well as efficacy thereof. Royal jelly (see Patent Document 1, for example), a plant, such as *Viburnum phlebotrichum* or the like, and an extract thereof (see Patent Document 2, for example), a *Curcumae rhizoma*-containing composition (see Patent Document 3, for example), a concentrate prepared from sake (see Patent Document 4, for example), and the like have been also known to be effective for liver diseases.

Patent Document 1: JP-A-2000-336038
Patent Document 2: JP-A-2004-346065
Patent Document 3: JP-A-2005-112846
Patent Document 4: JP-A-2006-306792

DISCLOSURE OF THE INVENTION

Problems to be Solved by the Invention

A decrease in liver function cannot be easily and conveniently prevented or ameliorated by known methods. Moreover, effects achieved by known methods are not necessarily satisfactory. Accordingly, an object of the present invention is to solve the above problems, and provide a liver function-protecting agent that has a high safety, and may easily and conveniently prevent or ameliorate a decrease in liver function via oral intake, and also provide a liver function-protecting food, drink, or feed that includes the liver function-protecting agent.

Means for Solving the Problems

In order to achieve the above object, the inventors of the present invention conducted extensive studies on a liver function-protecting agent that exhibits an efficacy of protecting the liver function, and found that a decrease in liver function can be prevented or ameliorated by oral intake of a phospholipid. This finding has led to the completion of the present invention in which the phospholipid is contained as an active ingredient. Specifically, the present invention provides as follows:

(1) A liver function-protecting agent comprising a phospholipid as an active ingredient.

(2) The liver function-protecting agent according to (1), wherein the phospholipid is derived from milk or a milk material.

(3) The liver function-protecting agent according to (2), wherein the milk or the milk material is any one among cow's milk, butter serum, and buttermilk.

(4) A liver function-protecting agent comprising a phospholipid-containing composition derived from milk or a milk material as an active ingredient.

(5) The liver function-protecting agent according to (4), wherein the phospholipid-containing composition includes the phospholipid in an amount of 10 wt % or more based on the total solid in the composition.

(6) The liver function-protecting agent according to (5), wherein the phospholipid-containing composition includes lactosylceramide in an amount of 0.16 wt % or more based on the total solid in the composition.

(7) The liver function-protecting agent according to (6), wherein the lactosylceramide is obtained by heating the milk or the milk material under acidic conditions.

(8) The liver function-protecting agent according to any one of (4) to (7), wherein the milk or the milk material is any one among cow's milk, butter serum, and buttermilk.

(9) A liver function-protecting food or drink comprising the liver function-protecting agent according to any one of (1) to (7).

(10) A liver function-protecting feed comprising the liver function-protecting agent according to any one of (1) to (7).

(11) A liver function-protecting food or drink comprising the liver function-protecting agent according to (8).

(12) A liver function-protecting feed comprising the liver function-protecting agent according to (8).

(13) A method for protecting liver function comprising administering a phospholipid in an amount of 283 mg/day or more.

(14) The method according to (13), wherein the phospholipid is derived from milk or a milk material.

Effects of the Invention

The liver function-protecting agent according to the present invention has an excellent effect of preventing or ameliorating a decrease in liver function. Since the liver function-protecting agent according to the present invention is prepared from milk or a milk material, the liver function-protecting agent according to the present invention is also excellent in safety. When administering an alcohol-containing feed containing the liver function-protecting agent according to the present invention to mice, a decrease in liver function may be significantly suppressed as compared with mice that were administered a feed that did not contain the liver function-protecting agent according to the present invention. An excellent liver function-protecting effect may be achieved by utilizing the present invention for arbitrary orally-taken products, such as food, supplement and the like. The liver function-protecting agent according to the present invention is very useful in the health-related markets.

BEST MODE FOR CARRYING OUT THE INVENTION

The present invention features that a phospholipid is used as an active ingredient. A chemically synthesized phospholipid or a phospholipid derived from a soybean, an egg yolk, or the like may be used as the phospholipid. It is preferable to use a phospholipid derived from milk or a milk material in particular.

Examples of the phospholipid derived from milk or a milk material that may be used in the present invention include phospholipids prepared from mammalian milk, such as cow's milk, goat's milk, ewe's milk, human's milk or the like.

Examples of milk or the milk material used in the present invention include, but not limited to, cow's milk, butter serum, buttermilk, and the like. The term "butter serum" refers to a light yellow liquid that is obtained when producing butter oil from butter or high-fat cream having a fat content of 60 wt % or more that is obtained by centrifuging cow's milk to produce a cream fraction having a fat content of 40 wt % or more, and increasing the fat content by centrifugation or the like again. Specifically, the term "butter serum" refers to an aqueous phase fraction having a fat content of 30 to 51 wt % that is obtained by subjecting the high-fat cream or butter to centrifugation, heating, or shear. The term "buttermilk" refers to a liquid that is obtained when producing butter from fermented cream or cream having a fat content of 40 wt % or more. Specifically, the term "butter serum" refers to an aqueous phase fraction having a fat content of 1 to 15 wt % that is discharged during butter production by subjecting the cream or fermented cream to shear.

The phospholipid-containing composition derived from milk or a milk material used in the present invention refers to a composition that is prepared from milk or a milk material, and may be a composition that includes a phospholipid in an amount of 10 wt % or more based on the total solid in the composition. The composition may be prepared by the following method.

Specifically, milk or a milk material is filtered through a microfiltration (MF) membrane or an ultrafiltration (UF) membrane to obtain a phospholipid-containing composition derived from milk or a milk material. It is preferable that the microfiltration (MF) membrane has a pore size of 0.1 to 2.0 μm when used in the method. If the pore size of the microfiltration (MF) membrane is less than 0.1 μm, foreign substances, such as whey proteins and the like, may remain in the concentrate so that the lipid content based on the solid of in the composition may decrease. As a result, the effects of the resulting liver function-protecting agent may deteriorate. If the pore size of the microfiltration (MF) membrane is more than 2.0 μm, fat globules may pass through the membrane (i.e., may leak into the filtrate), consequently the amount of liver function-protecting lipid fraction in the concentrate fraction may decrease. As a result, the effects of the resulting liver function-protecting agent may deteriorate. It is most preferable to use a microfiltration (MF) membrane having a pore size of about 0.1 to 2.0 μm taking account of the amount of proteins mixed therein and the recovery rate of phospholipids. As a microfiltration (MF) membrane having a pore size of 0.1 to 2.0 μm, "Membralox" (manufactured by SCT (Societe des Ceramiques Techniques)) may be used, for example. It is preferable that the ultrafiltration (UF) membrane have a molecular weight cut-off of 5 to 500 kDa. If the molecular weight cut-off of the ultrafiltration (UF) membrane is less than 5 kDa, lactose may also be concentrated and the lipid content may not unpreferably increase. 500 kDa of the molecular weight cut-off is the upper limit of the molecular weight cut-off of the ultrafiltration (UF) membrane.

Before filtering the raw material through the microfiltration (MF) membrane or the ultrafiltration (UF) membrane, it is preferable to adjust the pH of the raw material to 4.0 to 5.0 by adding an acid, and casein proteins may be removed by subjecting to isoelectric precipitation. This makes it possible to prevent the membrane from adhering grime during the treatment while increasing the lipid content based on the solid in the resulting concentrate.

Precipitation of casein proteins is further promoted by adding calcium chloride after adjusting the pH of the raw material to 4.0 to 5.0. Calcium chloride is preferably added in an amount of 0.01 to 0.05 wt % based on the total amount of the resultant. The type of acid that is added to adjust the pH of the raw material is not particularly limited, but an inorganic acid, such as hydrochloric acid, sulfuric acid or the like is preferably used.

The phospholipid-containing composition derived from milk or a milk material may preferably be recovered using a filter press, a decanter, or the like, but not particularly limited to. The concentrate obtained by the membrane treatment is preferably processed into a powder or paste by freeze-drying, spray-drying, or the like in order to facilitate storage, but not particularly limited to.

A composition that includes a phospholipid in an amount of 10 wt % or more based on the total solid in the composition can thus be prepared as a phospholipid-containing composition derived from milk or a milk material. Though other components in the composition may not particularly be limited, according to the above method, the resulting composition with 15 to 50 wt % of proteins, 10 to 50 wt % of carbohydrates, and 5 to 10 wt % of ash based on the total solid in the composition may be obtained. The composition has a water content of 5 wt % or less.

A composition that includes 10 wt % or more of a phospholipid and 0.16 wt % or more of lactosylceramide based on the total solid in the composition may also be used as the phospholipid-containing composition derived from milk or a milk material and may be suitably used for the liver function-protecting agent. This composition may be prepared by the following method, for example.

Specifically, milk or a milk material is heated under acidic conditions to convert ganglioside GD3 and/or ganglioside GM3 into lactosylceramide. A phospholipid-containing composition derived from milk or a milk material according to the present invention that contains a lactosylceramide may thus be obtained.

It is very important to appropriately adjust the pH and the temperature during the heat treatment. Specifically, the lower the pH is or the higher the temperature is, the larger the decomposition rate of lactosylceramide increases. However, the decomposition rate of lactosylceramide also increases as the pH decreases or the temperature increases. In order to produce lactosylceramide in high yield, it is preferable to adjust the pH to 3.0 to 5.0, and more preferably 3.0 to 4.0, and adjust the temperature to 70 to 100° C. under acidic conditions, for example. The treatment time that corresponds to the heat treatment conditions may be appropriately set within the range of 30 to 180 minutes while taking account of the production rate and the decomposition rate.

When heating a raw material derived from milk under low pH conditions of less than pH 3.0, a supernatant liquid is enfolded in by a precipitate, and the precipitate and the supernatant liquid may not be sufficiently separated each other when precipitating and removing casein which is a main protein, so that the yield of a lactosylceramide-containing fraction may decrease. Specifically, since casein has a small particle diameter and is stable protein at less than pH 3.0, precipitation may occur to only a small extent, and thus incomplete precipitation may occur while enfolding supernatant liquid in.

A phospholipid-containing composition derived from milk or a milk material which contains a lactosylceramide at a higher concentration may be obtained by filtering milk or a milk material through a microfiltration (MF) membrane or an ultrafiltration (UF) membrane. The microfiltration (MF) membrane used at the time preferably has a pore size of 0.1 to 2.0 µm. If the pore size of the microfiltration (MF) membrane is less than 0.1 µm, foreign substances, such as whey proteins or the like, may remain in the concentrate so that the effects of the resulting liver function-protecting agent may deteriorate due to decrease of the lipid content based on the solid. If the pore size of the microfiltration (MF) membrane is more than 2.0 µm, fat globules may pass through the membrane to leak into the filtrate, so that the amount of lipid fraction which has liver function-protecting effects may decrease in the concentrate fraction. As a result, the effects of the resulting liver function-protecting agent may deteriorate too. It is most preferable to use a microfiltration (MF) membrane having a pore size of about 0.1 to 2.0 µm taking account of the amount of proteins contaminated therein and the recovery rate of lactosylceramide. As the microfiltration (MF) membrane having a pore size of 0.1 to 2.0 µm "Membralox" (manufactured by SCT (Societe Des Ceramiques Techniques)) may be used, for example. It is preferable that the ultrafiltration (UF) membrane have a molecular weight cut-off of 5 to 500 kDa. If the molecular weight cut-off of the ultrafiltration (UF) membrane is less than 5 kDa, lactose may also be concentrated so that the lipid content may not unpreferably increase. 500 kDa of the molecular weight cut-off is the upper limit of the molecular weight cut-off of the ultrafiltration (UF) membrane.

Before filtering the raw material through the microfiltration (MF) membrane or the ultrafiltration (UF) membrane, it is preferable to adjust the pH of the raw material to 4.0 to 5.0 by adding an acid, and casein proteins may be removed by subjecting to isoelectric precipitation. This preferably makes it possible to prevent the membrane from adhering grime during the treatment while increasing the lipid content based on the solid in the resulting concentrate.

Precipitation of casein proteins is further promoted by adding calcium chloride after adjusting the pH of the raw material to 4.0 to 5.0. Calcium chloride is preferably added in an amount of 0.01 to 0.05 wt % based on the total amount of the resultant. The type of acid that is added to adjust the pH of the raw material is not particularly limited, but an inorganic acid, such as hydrochloric acid, sulfuric acid or the like is preferably used.

A composition that includes 10 wt % or more of a phospholipid and 0.16 wt % or more of lactosylceramide based on the solid in the composition can thus be prepared as a phospholipid-containing composition derived from milk or a milk material. Though other components in the composition may not particularly be limited, according to the above method, the resulting composition with 15 to 50 wt % of proteins, 10 to 50 wt % of carbohydrates, and 5 to 10 wt % of ash based on the total solid in the composition may be obtained. The composition has a water content of 5 wt % or less.

The above phospholipid and phospholipid-containing composition derived from milk or a milk material may be directly used as the liver function-protecting agent according to the present invention. Note that the phospholipid or the phospholipid-containing composition may be mixed with a raw material or the like, such as sugars, lipids, proteins, vitamins, minerals or flavor, that is normally used for food, drink, or feed, and the resultant mixture may be prepared into a powdered drug, granules, a tablet, a capsule, a drinkable preparation, or the like in accordance with conventional methods. After preparing the formulation, the resulting product may be added to a nutrient preparation, food or drink, such as yogurt, milk drinks or wafer, or feed.

The liver function-protecting agent according to the present invention exerts a liver function-protecting effect through oral intake of the phospholipid in an amount of 283 mg or more, and preferably 350 mg or more per kg of a mouse as shown in the hepatopathy model test described later. Therefore, a liver function-protecting effect is expected to be achieved when an adult takes the phospholipid in an amount of normally 283 mg/day or more, and preferably 350 mg/day or more according to an extrapolation method. The liver function-protecting agent may be administered so that the phospholipid can be taken in the above amount.

The liver function-protecting food or drink according to the present invention may be produced by adding the liver function-protecting agent according to the present invention to a normal food or drink, such as yogurt, milk-based drink, wafer, dessert or the like. It is preferable that the liver function-protecting food or drink is added with the liver function-protecting agent so that the amount of the phospholipid is 50 to 200 mg per 100 g of the food or drink depending on the form of the food or drink so as to take the phospholipid in an amount of 283 mg/day or more per adult per day. The liver function-protecting feed according to the present invention may be produced by adding the liver function-protecting agent according to the present invention to a normal feed, such as livestock feed, pet food or the like. It is preferable that the liver function-protecting feed is added with the liver function-protecting agent so that the amount of the phospholipid is 30 to 150 mg per 100 g of the feed so as to take the phospholipid in an amount of 283 mg/day or more.

The present invention is further described below by way of examples and test examples. Note that the following examples merely exemplify the present invention and should not be construed as limiting the present invention.

Example 1

A 20% solution of a butter serum powder (manufactured by Tatua) was prepared. The pH of the solution was adjusted to 4.5 by adding 5M hydrochloric acid. The solution was allowed to stand at 50° C. for one hour, and casein proteins were aggregated as precipitates. After removing the aggregates using a filter press, the resulting aqueous solution was filtered through a microfiltration (MF) membrane with a pore size of 1.4 µm (manufactured by SCT) to obtain a concentrated liquid fraction. After freezing the concentrated liquid fraction obtained as above, water was removed from the concentrated liquid fraction by freeze-drying to obtain a phospholipid-containing composition derived from milk or a milk material. The phospholipid-containing composition had a lipid content of 56 wt %, a protein content of 25 wt %, a carbohydrate content of 13 wt %, and an ash content of 6 wt % based on the total solid in the composition. The composition had a phospholipid content of 30 wt % based on the total solid in the composition.

Example 2

A 15% solution of a buttermilk powder (manufactured by Snow Brand Milk Products Co., Ltd.) was prepared. The solution was adjusted to pH 4.5 by adding 1M hydrochloric acid. The solution was allowed to stand at 40° C. for 30 minutes, and casein proteins were aggregated as precipitates. After removing the aggregates using a clarifier, the resulting supernatant liquid was filtered through a microfiltration (MF) membrane with a pore size of 0.1 µm (manufactured by SCT)

to obtain a concentrated liquid fraction. After freezing the concentrated liquid fraction obtained as above, water was removed from the concentrated liquid fraction by freeze-drying to obtain a phospholipid-containing composition derived from milk or a milk material. The phospholipid-containing composition had a lipid content of 50 wt %, a protein content of 27 wt %, a carbohydrate content of 16 wt %, and an ash content of 7 wt % based on the total solid in the composition. The composition had a phospholipid content of 20 wt % based on the total solid in the composition.

Example 3

10 wt % butter serum aqueous solution containing 230 mg/l ganglioside GD3 was adjusted to pH 3.0 by adding 15% hydrochloric acid. Calcium chloride was added to the solution in an amount of 0.03 wt % based on the total amount of the solution. The solution was heated at 88° C. for 180 minutes. The solution was then adjusted to pH 4.5 to 5.0 to aggregate casein which was the main protein in the raw material. The precipitate of casein was completely removed using a centrifuge (manufactured by Beckman) to obtain a supernatant liquid.

The supernatant liquid was neutralized with 10% potassium hydroxide, and filtered through a microfiltration membrane with a pore size of 0.1 µm (manufactured by Milipore) to obtain a concentrated liquid. The concentrated liquid was dried using freeze-drying to obtain a phospholipid-containing composition derived from milk or a milk material including a lactosylceramide.

The lipid content in the resulting composition measured by the Roese-Gottlieb method was 50 wt %. The phospholipid-containing composition derived from milk or a milk material included the lactosylceramide in amount of 36 mg/g according to the quantitative determination by HPLC.

The phospholipid-containing composition had a lipid content of 56 wt %, a protein content of 25 wt %, a carbohydrate content of 13 wt %, and an ash content of 6 wt % based on the total solid in the composition. The composition had a phospholipid content of 33 wt % and a lactosylceramide content of 3.6 wt % based on the total solid in the composition.

Example 4

A ganglioside-containing material containing 360 mg/l of ganglioside GM3 was prepared from butter serum in accordance with a method of producing ganglioside GM3 by acid-hydrolyzing ganglioside GD3 (JP-A-H05-279379). 10% aqueous solution of the ganglioside material was adjusted to pH 3.0 by adding 15% hydrochloric acid. Calcium chloride was added to the solution in an amount of 0.03 wt % based on the total amount of the solution. The solution was heated at 88° C. for 180 minutes. The solution was then adjusted to pH 4.5 to 5.0 to aggregate casein which was the main protein in the raw material. The precipitate of casein was completely removed using a centrifuge (manufactured by Beckman) to obtain a supernatant liquid.

The supernatant liquid was neutralized with 10% potassium hydroxide, and filtered through a microfiltration membrane with a pore size of 0.1 µm (manufactured by Milipore to obtain a concentrated liquid. The concentrated liquid was dried by freeze-drying to obtain a phospholipid-containing composition derived from milk or a milk material including lactosylceramide.

The lipid content in the resulting composition measured by the Roese-Gottlieb method was 50 wt %. The phospholipid-containing composition derived from milk or a milk material included the lactosylceramide in amount of 39 mg/g according to the quantitative determination by HPLC. The phospholipid-containing composition had a lipid content of 56 wt %, a protein content of 25 wt %, a carbohydrate content of 13 wt %, and an ash content of 6 wt % based on the total solid in the composition. The composition had a phospholipid content of 29 wt % and a lactosylceramide content of 3.9 wt % based on the total solid in the composition.

Test Example 1

Animal Experiments

The liver function-protecting effect of a phospholipid was evaluated using the phospholipid-containing compositions derived from milk or a milk material which was obtained in Examples 1 to 4 and a commercially available soybean-derived phospholipid ("LP-20P" manufactured by the Nisshin OilliO Group, Ltd.). C57BL/6 male mice were used for the experiments. After one-week preliminary feeding, the mice (7 weeks old) were divided into a group that was administered an alcohol-containing liquid feed shown in Table 1 (control group), a group that was administered a feed prepared by adding the phospholipid-containing composition derived from milk or a milk material obtained in Example 1 to the alcohol-containing liquid feed shown in Table 1 so that the amount of the phospholipid was 283 mg per kg of the mouse (group A), a group that was administered a feed prepared by adding the phospholipid-containing composition derived from milk obtained in Example 2 to the alcohol-containing liquid feed shown in Table 1 so that the amount of the phospholipid was 350 mg per kg of the mouse (group B), a group that was administered a feed prepared by adding the phospholipid-containing composition derived from milk obtained in Example 3 to the alcohol-containing liquid feed shown in Table 1 so that the amount of the phospholipid was 500 mg per kg of the mouse (group C), a group that was administered a feed prepared by adding the phospholipid-containing composition derived from milk obtained in Example 4 to the alcohol-containing liquid feed shown in Table 1 so that the amount of the phospholipid was 800 mg per kg of the mouse (group D), and a group that was administered a feed prepared by adding a commercially available soybean-derived phospholipid to the alcohol-containing liquid feed shown in Table 1 so that the amount of the phospholipid was 600 mg per kg of the mouse (group E). The mice were allowed free access to the feed for one week. The mice were also allowed free access to water. After one week, blood was collected from each mouse, and serum was sampled from the collected blood by a conventional method. The contents of glutamate oxaloacetate transaminase ("GOT") and glutamate pyruvate transaminase ("GTP") in the serum were measured using a measurement kit manufactured by FujiFilm Corporation. GOT is an enzyme necessary for synthesis of amino acids, and is contained mainly in heart muscle, liver, skeletal muscle, kidney, or the like. A liver disease (e.g., acute or chronic hepatitis, fatty liver, etc.) is suspected when the GOT level is high. GPT is also an enzyme (transaminase) necessary for synthesis of amino acids, and is contained in liver to a large extent. A liver disease, such as acute or chronic hepatitis, fatty liver, alcoholic hepatitis or the like, is suspected when the GPT level is high. The results are shown in Table 2.

TABLE 1

| | |
|---|---|
| Protein (derived from cheese) | 5.2 (wt %) |
| Fat (derived from cheese) | 5.1 |
| Sucrose | 8.6 |
| Ethanol | 5.1 |
| Xanthan gum | 0.1 |
| Water | 75.9 |

TABLE 2

| Group | GOT (mg/dl) | GPT (mg/dl) |
|---|---|---|
| Control | 93.2 | 45.3 |
| A | 52.3 | 8.9 |
| B | 57.2 | 8.5 |
| C | 53.3 | 9.1 |
| D | 55.5 | 8.3 |
| E | 54.2 | 8.7 |

No significant difference in feed intake was observed among the groups A to E. A significant difference in GOT level or GTP level in the serum was observed among the groups A to E. The groups A to D that were administered the feed containing the phospholipid-containing composition derived from milk or a milk material obtained in Examples 1 to 4 and the group E that was administered the feed containing the soybean-derived phospholipid had a significantly lower GOT level and GTP level as compared with the control group. Specifically, a liver function-protecting effect was observed.

Example 5

250 g of the phospholipid-containing composition derived from milk or a milk material which was obtained in Example 1 was dissolved in 4750 g of deionized water. The solution was heated to 50° C., and stirred at 6000 rpm for 30 minutes using a TK-homomixer ("TK ROBO MICS" manufactured by PRIMIX Corporation) to obtain a phospholipid solution containing phospholipid derived from milk or milk material in a concentration of 2500 g/100 g. 4.0 kg of the resulting phospholipid-containing composition derived from milk or a milk material was added with 5.0 kg of casein, 5.0 kg of a soybean protein, 1.0 kg of fish oil, 3.0 kg of perilla oil, 18.0 kg of dextrin, 6.0 kg of a mineral mixture, 1.95 kg of a vitamin mixture, 2.0 kg of an emulsifying agent, 4.0 kg of a stabilizer, and 0.05 kg of flavor to. A retort pouch (200 ml) was charged with the mixture. The mixture was then sterilized at 121° C. for 20 minutes using a retort sterilizer (Class 1 pressure vessel, "RCS-4CRTGN" manufactured by Hisaka Works, Ltd.) to produce 50 kg of a liver function-protecting nutrient composition containing the liver function-protecting agent according to the present invention. The liver function-protecting nutrient composition contained the phospholipid derived from milk or a milk material which was active ingredient of liver function-protecting agent in an amount of 100 mg/100 g.

Example 6

2 g of an acidifier was dissolved in 700 g of deionized water. 10 g of the phospholipid-containing composition derived from milk which was obtained in Example 2 was dissolved in the solution. The resulting solution was heated to 50° C., and stirred at 9500 rpm for 30 minutes using an ultra-disperser ("ULTRA-TURRAX T-25" manufactured by IKA Japan K.K.). After the addition of 100 g of maltitol, 20 g of reduced starch syrup, 2 g of flavor, and 166 g of deionized water, a glass bottle (100 ml) was charged with the mixture. After sterilization at 90° C. for 15 minutes, the bottle was tightly sealed. Ten bottles (100 ml) of a liver function-protecting drink containing the liver function-protecting agent according to the present invention were thus obtained. The liver function-protecting drink contained the phospholipid derived from milk or a milk material (active ingredient of liver function-protecting agent) in an amount of 200 mg/100 g.

Example 7

2 kg of the phospholipid-containing composition derived from milk which was obtained in Example 4 was dissolved in 98 kg of deionized water. The solution was heated to 50° C., and stirred at 3600 rpm for 40 minutes using a TK-homomixer ("TK ROBO MICS" manufactured by Tokushu Kika Kogyo Co., Ltd.) to obtain a phospholipid solution derived from milk or milk material which included phospholipid derived from milk in a concentration of 510 mg/100 g). 12 kg of soybean meal, 14 kg of powdered skim milk, 4 kg of soybean oil, 2 kg of corn oil, 23.2 kg of palm oil, 14 kg of corn starch, 9 kg of flour, 2 kg of bran, 5 kg of a vitamin mixture, 2.8 kg of cellulose, and 2 kg of a mineral mixture were added to 10 kg of the milk-derived phospholipid solution. The mixture was sterilized at 120° C. for 4 minutes to prepare 100 kg of a liver function-protecting dog food containing the liver function-protecting agent according to the present invention. The liver function-protecting dog food contained the phospholipid derived from milk or a milk material (active ingredient of liver function-protecting agent) in an amount of 51 mg/100 g.

Example 8

Raw materials were mixed in a ratio shown in Table 3. 1 g of the mixture was formed and tableted by a conventional method to produce a liver function-protecting agent according to the present invention. The liver function-protecting agent contained the phospholipid derived from milk or a milk material (active ingredient) in an amount of 55 mg/g.

TABLE 3

| Crystalline glucose hydrate | 83.5 (wt %) |
|---|---|
| Phospholipid-containing composition (Example 1) | 10.0 |
| Mineral mixture | 5.0 |
| Sugar ester | 1.0 |
| Flavor | 0.5 |

The invention claimed is:

1. A method, comprising:
   heating milk or milk material under acidic conditions to convert GD3 ganglioside and GM3 ganglioside contained in the milk into lactosylceramide and to thereby form a composition comprising a liver function-protecting agent; and
   administering the composition comprising the liver function-protecting agent to a mammal to improve liver function in the mammal;
   wherein the liver function-protecting agent comprises (1) at least 10 percent by weight of a phospholipid, and (2) at least 0.16 percent by weight of lactosylceramide.

2. The method of claim 1, wherein the amount of the liver function-protecting agent administered is 283 milligrams or more of phospholipid per day.

3. The method of claim 1, wherein the phospholipid is a chemically synthesized phospholipid or a naturally-derived phospholipid.

4. The method of claim 1, wherein the composition is formulated in a human food product, a drink product, or an animal feed product.

5. The method of claim 4, wherein the composition comprises 0.05 to 0.2 percent by weight of phospholipid.

6. The method of claim 4, wherein the composition comprises 0.03 to 0.15 percent by weight of phospholipid.

* * * * *